US010912656B2

(12) United States Patent
Müller (10) Patent No.: US 10,912,656 B2
(45) Date of Patent: Feb. 9, 2021

(54) MODULAR SURGICAL INSTRUMENT (71) Applicant: Erich Johann Müller, Kleinwallstadt (DE)

(72) Inventor: Erich Johann Müller, Kleinwallstadt (DE)

(*) Notice: Subject to any disclaimer, the term of this patent is extended or adjusted under 35 U.S.C. 154(b) by 245 days.

(21) Appl. No.: 16/159,609

(22) Filed: Oct. 12, 2018

(65) Prior Publication Data

US 2019/0374349 A1    Dec. 12, 2019

(30) Foreign Application Priority Data

Jun. 6, 2018  (DE) .................... 20 2018 103 170 U
Jun. 11, 2018 (EP) ..................................... 18177063

(51) Int. Cl.
*A61F 2/46* (2006.01)
*A61F 2/32* (2006.01)

(52) U.S. Cl.
CPC ..... *A61F 2/4607* (2013.01); *A61F 2002/4619* (2013.01); *A61F 2002/4627* (2013.01); *A61F 2002/4628* (2013.01)

(58) Field of Classification Search
CPC ........ A61F 2/4607; A61F 2/46; A61F 2/4603; A61F 2002/4627–4628; A61F 2002/4619
USPC ...................... 606/99–100; 623/20.35–20.36, 623/22.15–22.2
See application file for complete search history.

(56) References Cited

U.S. PATENT DOCUMENTS

| 4,222,382 A * | 9/1980 | Antonsson | A61F 2/4607 606/100 |
| 2010/0121331 A1* | 5/2010 | Sharp | A61F 2/4607 606/80 |

(Continued)

FOREIGN PATENT DOCUMENTS

| DE | 4332872 C1 | 4/1995 |
| DE | 29508578 U1 | 8/1995 |
| DE | 102009024654 A1 | 12/2010 |

(Continued)

OTHER PUBLICATIONS

Xtract-All Hip Surgical Technique Guide, Shukla Medical, Jan. 1, 2018.

(Continued)

*Primary Examiner* — Jessica Weiss
(74) *Attorney, Agent, or Firm* — Barry E. Bretschneider; Whiteford Taylor & Preston, LLP (57) ABSTRACT

A modular surgical instrument for knocking out or implanting a prosthesis that defines a prosthesis axis and which has a prosthesis neck includes a tool head with a passthrough for accommodating the prosthesis neck, a locking device for locking the mounted prosthesis neck, and a chuck, which has an axis for transferring a clamping force for the locking device. The passthrough and the chuck are arranged on opposite ends of the tool head relative to a lengthwise direction defined by the axis of the chuck, wherein the passthrough defines a passthrough axis which coincides substantially with the prosthesis neck axis when the prosthesis neck is locked in place. The axis of the chuck is at a distance from a plane defined by the lengthwise direction and the passthrough axis and/or is at a distance from a passthrough lengthwise axis that extends in the lengthwise direction and through the passthrough.

9 Claims, 3 Drawing Sheets

(56) References Cited

U.S. PATENT DOCUMENTS

2010/0331902 A1* 12/2010 Biegun ................ A61F 2/4607
606/86 R
2017/0367714 A1* 12/2017 McCulloch ........... A61F 2/4607

FOREIGN PATENT DOCUMENTS

| EP | 2363076 A1 | 9/2011 |
| EP | 2363098 A1 | 9/2011 |
| FR | 2742334 A1 | 6/1997 |

OTHER PUBLICATIONS

James Gilroy, Shukla—Hip Stem Extractor Demonstration Video, URL:https://www.youtube.com/watch?v=EEWrMjquKoc, Youtube, Apr. 4, 2013.

* cited by examiner

MODULAR SURGICAL INSTRUMENT

CROSS REFERENCE TO RELATED APPLICATIONS

The present application claims the benefit of German Utility Model Application No. 20 2018 103 170.8 filed on Jun. 6, 2018 and European Patent Application No. 18177063.7 filed on Jun. 11, 2018. All the above are hereby incorporated by reference.

FIELD OF THE INVENTION

The present invention relates to a universal, modular surgical instrument for driving out or implanting artificial prostheses and joint prostheses, particularly hip prostheses, which may be used in various minimal surgery access methods.

BACKGROUND OF THE INVENTION

Procedures for implanting artificial joint prostheses, to replace hip, knee or shoulder joints for example, have been established for several decades. In Germany alone, about 400,000 hip and knee prostheses have been implanted yearly. The useful life of artificial prostheses is limited by infections, aseptic loosening and breaks. Thus, the average useful life of a prothesis is about 10 to 15 years, and the incidence of surgical corrections in the first 10 years after implantation of a prosthesis is about 10%. Consequently, it is essential to replace prostheses, in which case as far as possible force should only be applied in a direction along an axis of the prosthesis to avoid damaging adjacent bones with transverse forces.

When implanting or replacing artificial prostheses, a minimally invasive surgical procedure is preferred, so that skin incisions and more extensive damage to the soft tissue are avoided or limited. Minimally invasive procedures have become widely accepted for hip joint replacements because they make it possible to avoid making long incisions in the skin, detaching muscles and causing extensive damage to the soft tissue that surrounds the joint.

For example, the muscle groups on the sides of the hips that are important for walking are treated gently in minimally invasive operations, so the patient can be mobilised, i.e., he can stand and walk, faster and with less pain after the operation. Long-term irritations of the surrounding bursae and soft tissue calcifications also occur less frequently after hip prosthesis operations using a minimally invasive access route.

The access route in minimally invasive hip prosthesis operations for example has shifted from an initially posterior to a progressively more lateral and finally to a frontal access, so that nowadays these 3 primary access routes are used roughly equally in all minimally invasive procedures. Accordingly, it has become necessary to renew and adapt the tools that are used in the operations.

Surgical tools are known which consist of an actuating device of complex structure consisting of many individual parts with a control device connected closely thereto for fixing the prosthesis. However, they provide the surgeon with only a constricted working space and field of vision, increasing the potential for error in procedures for inserting and removing the prosthesis.

A knocking out tool with a tool head which has an opening in the centre to receive a prosthesis neck is known from DE 4332872 C1 for example. Displaceable actuators are arranged on the receiver in the tool head and can be displaced using a connected pressure rod to clamp a prosthesis neck firmly in place in the receiving opening. In DE 29508578 U1, a tool component for such a knocking out tool is disclosed in which actuators can be adjusted with an axially displaceable pressure rod. The head of the tool part is closed at the sides.

The object of the present invention is therefore to create a modular, universally usable knocking out instrument for various access routes, with different tool heads which assure secure clamping of different prosthesis necks. A further object, based thereon, consists in ensuring that the extraction force is exerted only in the axial direction of the prosthesis, and that an adequate working space is available to enable prostheses to be removed and inserted without permitting any potential damage to the prosthesis bone bed or other errors.

SUMMARY OF THE INVENTION

The object is solved according to the invention with a modular surgical instrument. The object according to the invention is further solved with an impact frame for a modular surgical instrument.

The modular surgical instrument for knocking out or implanting a prosthesis which defines a prosthesis axis and has a prosthesis neck that defines a prosthesis neck axis which does not extend parallel to the prosthesis axis, comprises a tool head with a passthrough for accommodating the prosthesis neck, a locking device for locking the mounted prosthesis neck, and a chuck with an axis for transferring a clamping force for the locking device, wherein the passthrough and the chuck are arranged at opposite ends of the tool heads in respect of a lengthwise direction defined by the chuck axis, and wherein the passthrough defines a passthrough axis which is substantially coincident with the prosthesis neck axis when the prosthesis neck is locked; wherein the axis of the chuck is at a distance from the plane defined by the lengthwise direction and the passthrough axis and/or the axis of the chuck is at a distance from a passthrough longitudinal axis which extends in lengthwise direction and through the passthrough.

According to one aspect of the present invention, the distance between the chuck axis and the plane defined by the lengthwise direction and the passthrough axis may be in the range from 0 cm-20 cm, preferably 5 cm-15 cm, and/or the distance between the chuck axis and the chuck from the passthrough longitudinal axis may be in the range from 0 cm-20 cm, preferably 5 cm-15 cm.

According to a further aspect, the modular surgical instrument may further comprise a clamping assembly which is connected detachably to the tool head by the chuck and which includes a clamping element for applying a clamping force and actuators for transferring the clamping force.

According to a further aspect the modular surgical instrument may further comprise an impact frame which is detachably connected to the clamping assembly, and which has a first connection device with a first axis for an impacting device for transferring an impact force.

According to a further aspect the modular surgical instrument may further comprise the impacting device, which is attached to the first connection device, wherein the impacting device comprises an impact plate, particularly a flat impact plate, or a slide hammer, and is aligned in such manner that the impact force acts along the first axis.

According to a further aspect, the impacting device may comprise a concave impact plate.

According to a further aspect, the first connection device or a fixed connection may be arranged in the lengthwise direction when viewed from the passthrough so that the first axis coincides with the prosthesis axis then the prosthesis neck is locked.

According to a further aspect, the impact frame may comprise a first and a second leg, wherein the first connection device or a fixed connection, preferably the connection device, is arranged on one end of the first leg with the first axis for the impacting device; wherein a second connection device or a fixed connection, preferably the connection device, is arranged on one end of the second leg with a second axis parallel to the first axis for the clamping assembly; and wherein a space between the ends of the legs is left free in the direction of the first and second axes.

According to a further aspect, the first axis and the second axis can be kept at a distance from each other.

According to a further aspect, the impact frame may be in the shape of an "L", wherein the clamping assembly is connected detachably to a second leg of the L shape by means of a second connection device or a fixed connection, and the first connection device or a fixed connection for the impacting device is arranged on a first leg of the L shape.

According to a further aspect, the locking device may comprise a blocking element that engages movably in the passthrough to lock the prosthesis neck, wherein the passthrough axis extends substantially perpendicularly to a direction of movement of the blocking element.

The impact frame for a modular surgical instrument for knocking out or inserting a prosthesis which defines a prosthesis axis and has a prosthesis neck which defines a prosthesis neck axis that does not extend parallel to the prosthesis axis has a first and a second leg; wherein a first connection device with a first axis for an impacting device is arranged on one end of the first leg; wherein a second connection device with a second axis parallel to the first axis for a clamping assembly is arranged on one end of the second leg; and wherein a space in the direction of the axes is left free between the ends of the legs (i.e. between the end of the first leg and the end of the second leg).

The first axis and the second axis can be kept at a distance from each other.

According to a further aspect of the impact frame, the distance between the first axis and the second axis may be in the range from 0 cm-20 cm, preferably 5 cm-15 cm.

According to a further aspect, the impact frame may comprise several frame sections, wherein the first leg and the second leg form frame sections, the ends of which extend substantially perpendicularly to the first and second axes, and wherein at least a part of the further frame sections which connect the first leg and the second leg extend in the direction defined by the first and second axes.

According to a further aspect of the impact frame, a third connection device which preferably comprises a passthrough hole on the impact frame may also be arranged on the first leg with a third axis for an impacting device, wherein the third axis coincides with the second axis.

According to a further aspect of the impact frame, an impact plate or a slide hammer may be attached to the first connection device.

According to a further aspect of the impact frame, a concave impact plate may be attached to the first connection device.

According to a further aspect of the impact frame, the first and/or second connection device may each comprise a passthrough hole in the impact frame.

According to a further aspect of the impact frame, an elastomer bushing, preferably made from silicone, may be arranged in the passthrough hole or each of the passthrough holes.

According to a further aspect of the impact frame, the first and/or second connection device comprise(s) a connecting screw which passes through the connecting hole and is secured with a nut.

According to a further aspect of the impact frame, the nut may be a hemispherical nut which is mounted in a hemispherical nut bed on the impact frame.

According to a further aspect, the impact frame may be in a "C" shape.

BRIEF DESCRIPTION OF THE DRAWINGS

In the following section, exemplary embodiments of the present invention will be described in greater detail with reference to the figures, wherein.

The same reference signs are used for identical or similar elements or components in both the description and the drawing. A list of reference signs is also provided, which applies for all figures. The variants represented in the figures are diagrams only, and do not necessarily represent actual dimensional proportions.

DETAILED DESCRIPTION OF THE INVENTION

Figure 1:
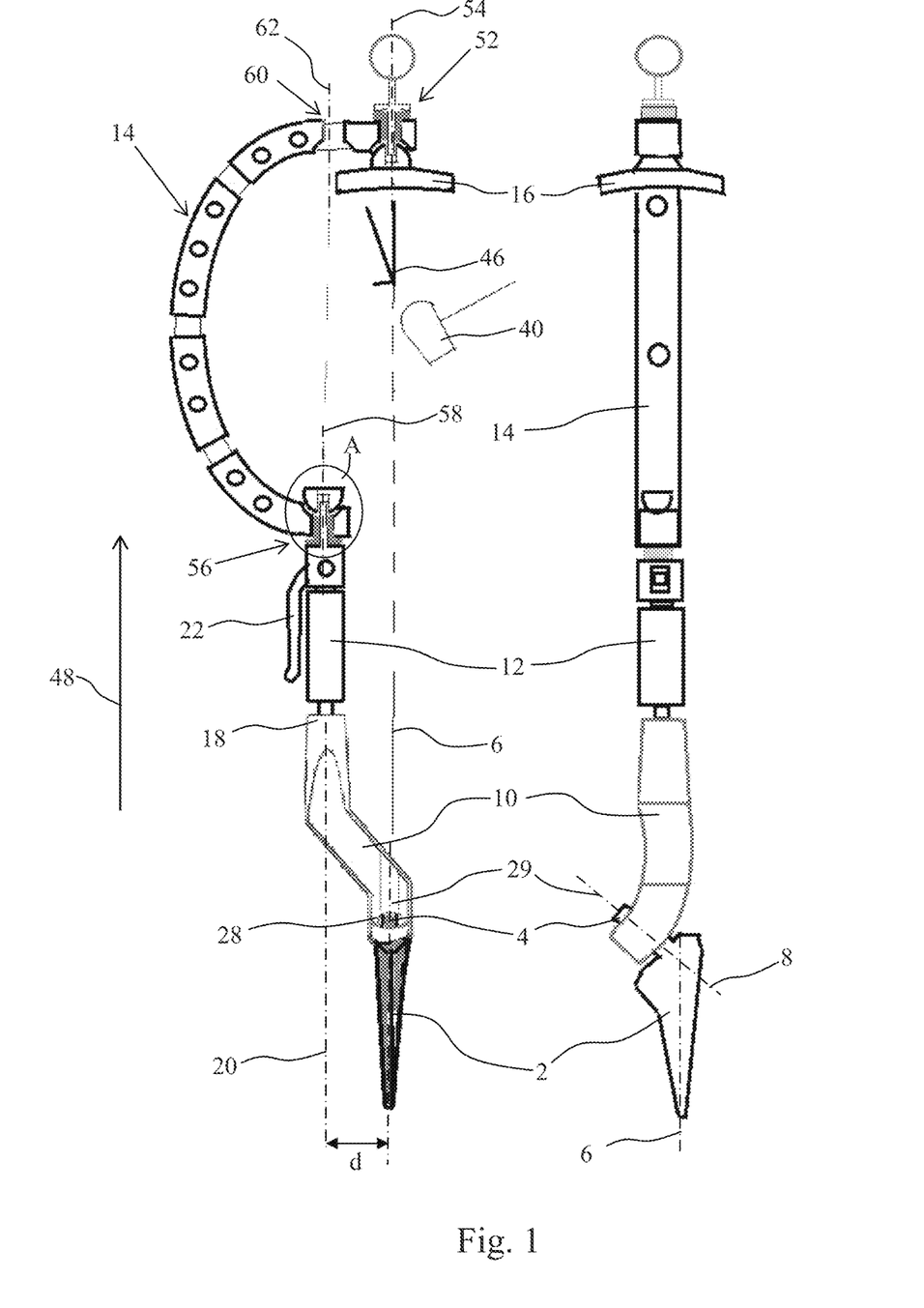
FIG. 1 shows a front and side view of modular surgical instrument according to the invention.

FIG. 1 represents a modular surgical instrument according to the invention (hereinafter also referred to simply as the instrument, the modular instrument or the surgical instrument) including optional elements, wherein the illustration on the left shows a frontal view and the illustration on the right a side view, and wherein a prosthesis is shown secured in place. The surgical instrument is intended for use in knocking out or inserting, mainly for knocking out artificial prostheses, particularly joint prostheses, such as hip, knee and/or shoulder prostheses. Such a prosthesis 2, having a prosthesis neck 4 is illustrated in the figure. Prosthesis 2 defines a prosthesis axis 6, the direction of which corresponds to the direction in which the prosthesis 2 is to be knocked out or inserted. In the same way, the prosthesis neck 4 defines prosthesis neck axis 8, which extends in a direction that is not parallel to prosthesis axis 6.

The modular surgical instrument represented in FIG. 1 comprises a tool head 10 which has an "offset", preferably a "lateral offset", as shown in the frontal view of the instrument in the left side of the figure, obviating the need to make a large incision on prosthesis axis 6 to gain access to the operation site, above prosthesis 2 in the figure, thus making minimally invasive access possible. This "offset" will be described in greater detail subsequently.

Figure 2:
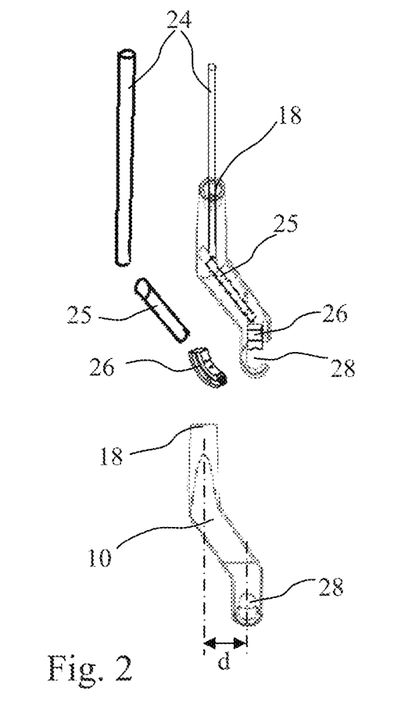
FIG. 2 shows a tool head according to the invention for a modular surgical instrument and associated actuators.

Tool head 10 as shown in FIG. 2 has a passthrough 28 on one end for accommodating the prosthesis neck 4, which is locked in place by a locking device. Passthrough 28 defines a passthrough axis 29 (in the direction of the passthrough). Typically, the (peripheral) border of the passthrough is substantially annular, the passthrough axis then corresponds to the central axis of the annular shape, i.e. it extends perpendicularly to the plane in which the annular shape lies. In this context, the term "annular" is used in a general sense, that is to say not necessarily in the form of a circular ring, for example it may enclose an oval or rectangular or polygonal shape. Passthrough 28 is designed such that when prosthesis neck 4 is locked in place (as in the figure) the passthrough axis 29 substantially coincided with the prosthesis neck axis 8; the formulation "substantially" is intended to indicate that a small angle of up to 15° may exist between the two axes, and a small distance of up to 10% of a prosthesis neck diameter may exist between the two axes.

The passthrough may be open at the side to make it possible and easier to accommodate the prosthesis neck. The rim of the passthrough is then typically in the form of a ring segment.

Tool head 10 further comprises a locking device which serves to lock (clamp) the mounted prosthesis neck 4 with a clamping force. The locking device may comprise a blocking element 26 which engages movably in the passthrough 28 and is guided in lateral grooves. The blocking element 26 is movable substantially perpendicularly to the passthrough axis 29, so that a cross section of the passthrough 28 can be modified and the prosthesis neck 4 can be locked or clamped in place by the application of a clamping force. The clamping force for the locking device is transferred at a chuck 18, and from there to the locking device; e.g., via actuators 24, 25 as illustrated in FIG. 2.

Chuck 18 has an axis 20 which defines a lengthwise direction 48. Passthrough 28 and chuck 18 are arranged on opposite ends of the tool head 10 relative to the lengthwise direction 48. There is preferably angle of approximately 45° or approximately 135° ("approximately" means that variations of up to 5° are possible) between the passthrough axis 29 and the lengthwise direction 48. The parallel displacement of passthrough axis 29 in lengthwise direction 48 defines a plane (perpendicular to the plane of the drawing in the frontal view on the left side of FIG. 1). The lateral offset is then manifested in that the axis 20 of chuck 18 does not lie in this plane, that is to say a distance d is present between the axis 20 of chuck 18 and the plane that is defined by lengthwise direction 48 and passthrough axis 29. (In the frontal view, the axis 20 of chuck 18 is for example offset to the left of the plane which is defined by lengthwise direction 48 and passthrough axis 29; of course, it might also be offset to the right.) In this way, the chuck 18 and the components that apply the clamping force are located outside of the operation site both in lengthwise direction 48 and in the lateral direction (transversely to the lengthwise direction). Distance d between the axis 20 der of chuck 18 and the plane defined by lengthwise direction 48 and passthrough axis 29 is preferably at least 2 cm, more preferably at least 5 cm. Distance d is preferably in the range from 2 cm-20 cm, more preferably in the range from 5 cm-15 cm, more preferably still in the range from 5 cm-10 cm.

The chuck is thus offset laterally from the passthrough relative to the plane defined by the passthrough axis and the lengthwise direction. An offset parallel to this plane or within this plane which may also exist in addition to or without the above. For example, a passthrough lengthwise axis extending through passthrough 28 and in lengthwise direction 48 (that is to say one which differs from passthrough axis 29), may lie within the plane defined by the passthrough axis 29 and the lengthwise direction 48 and still be located at a distance from the axis 20 of chuck 18. In such a case, in the frontal view of FIG. 1, an offset perpendicular to the plane of the drawing would exist; an example of a corresponding tool head is shown in the second image from bottom in FIG. 4. A lateral offset clearly suggests such a distance. This distance between passthrough lengthwise axis and axis 20 of the chuck is preferably also at least 2 cm, more preferably at least 5 cm, and is preferably in the range from 2 cm-20 cm, more preferably in the range from 5 cm-15 cm, still more preferably in the range from 5 cm-10 cm.

FIG. 1 further shows an optional clamping assembly (or clamping frame) 12, i.e. an assembly designed to create a clamping force which is connected detachably to the chuck with tool head 10; the term "optionally" is used here because in principle the clamping assembly may also be integrated with the tool head and/or the impact frame 14 (as discussed below), but a modular construction is preferred. The clamping force is applied by means of a clamping element and transferred to the tool head 10 via actuators. For example, the clamping force may be generated by means of an actuatable clamping lever 22 with an eccentric lever head (not shown) which acts on an actuator.

Clamping assembly 12 has an axis which coincides with axis 20 of chuck 20 when the clamping assembly 12 is connected to tool head 10 on chuck 18, so that the offset is transferred to the clamping assembly 12, and the clamping assembly 12, which is typically a component of elongated construction, does not protrude into the operating site. The clamping assembly 12 may also be configured to enable a variable preset displacement of the locking device (i.e., an adjustable displacement of the locking device before application of the actual clamping force which clamps the prosthesis neck in place) so that it may be used for various prosthesis necks with different dimensions and/or diameters. In the example given above, an adjustment thread may be provided in the clamping assembly, so that the distance between the clamping lever 22 and the chuck 18 can be changed, exerting a preload on the actuator.

An impact frame 14 is also represented in FIG. 1, in this case for example in a "C" shape, which is connected detachably to clamping assembly 12 and has a first connection device 52 with a first axis 54 for an impacting device for transferring an impact force which is generated with the aid of the impacting device and is intended to act along the first axis 54, wherein the impacting device is connected to the impact frame via the first connection device. The impact frame 14 is optional, since the impacting device might also be attached directly to the clamping assembly 12 or integrated therein (see FIG. 5h, for example). The impact frame according to the invention may be used together with a tool head with offset (FIG. 5a-FIG. 5c) or independently thereof, for example the impact frame may also be coupled with conventional tool heads of various types (FIG. 5d-FIG. 5g).

The impacting device may comprise for example an impact plate 16, which may in particular be flat or level, but is preferably concave (as represented in FIG. 1), a slide hammer 42 (see FIG. 5h and FIG. 5i) or a pneumatic impact machine. An impact plate 16 is struck with a hammer 40, for example, to create the impact force. A concave impact plate 16, that is to say one that is curved in concave manner (e.g., corresponding to a portion of a spherical surface of a ball as seen from the inside of the ball) is advantageous, since the hammer blow is necessarily centred thereby.

The detachable connection of the clamping assembly 12 to the impact frame 14 is made by means of a second connection device 56 with a second axis 58, wherein in the connected state the second axis 58 coincides with the axis of the clamping assembly 12 and consequently with axis 20 of chuck 18 as well. The first axis 54 and the second axis 58 are preferably parallel and at a distance from each other, more preferably the first connection device 52 should be arranged approximately in lengthwise direction 48 when viewed from passthrough 28, so that the when the prosthesis neck 4 is locked in position the first axis 54 substantially coincides with the prosthesis axis 6 of the prosthesis 2 locked in position on the prosthesis neck 4.

The distance between the first and second axes preferably corresponds to the distance d between the axis 20 of chuck 18 and the plane defined by the lengthwise direction 48 and the passthrough axis 8, that is to say it is preferably at least 2 cm, more preferably at least 5 cm. Similarly, the distance between the two axes is preferably in the range from 2 cm-20 cm, more preferably 5 cm-15 cm, still more preferably in the range from 5 cm-10 cm. In this way, the first axis 54, along which the impact force acts, coincides with the prosthesis axis 6, along which the prosthesis 2 is to be knocked out or implanted; consequently, transverse forces which would be generated by the lateral offset of tool head 10 and which might cause damage to the bone, for example, only arise to a very limited degree, if at all, and may be minimised further by corresponding design of the connection devices.

A first option for achieving this, as indicated in FIG. 5*i*, comprises an L-shaped impact frame. A first leg of the L-shape, on which the first connection device is arranged, extends along the first axis. The clamping assembly 12 is connected detachably to a second leg of the L-shape. The impacting device 16, for example a slide hammer 42, may be attached to the connection device as an extension of the first leg of the L-shape.

A preferred second embodiment of the impact frame comprises an impact frame 14 having a first and a second leg, wherein the first connection device 52 with the first axis 54 is arranged on an end of the first leg, and the second connection device 56 with the second axis 58 is arranged on an end of the second leg. (Note: The legs in this second option are described only as "legs" as distinct from the "legs of the L-shape" described in the previous, first option.) The first axis 54 and the second axis 58 extend parallel and at a distance from each other; the first connection device 52 is provided for fastening the impacting device 16, and the second connection device 56 is provided for fastening the clamping assembly 12. A space between the ends of the legs is left free in the direction of the two axes 54, 58, so that this space is available for the operator; in order to strike an impact plate 16 with a hammer 40, for example, as shown in the figures.

In the second embodiment of the impact frame, a third connection device 60 with a third axis 62 is preferably arranged on the first leg, and particularly in such manner that the third axis 62 coincides with the second axis 58. This makes it possible for a corresponding impact frame also to be used in conjunction with tool heads that do not have a lateral offset; see also FIG. 5*d*, FIG. 5*e* and FIG. 5*f*. According to the invention, the impact frame according to the second embodiment of the impact frame may thus be used regardless of whether the tool head has an offset. The third connection device may be constructed similarly to the first and second connection devices; see below.

Figure 6:
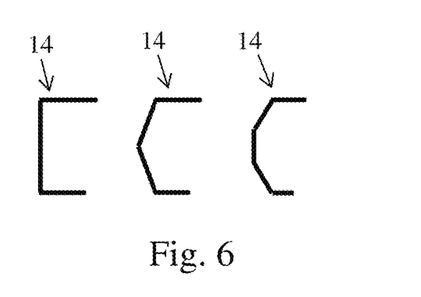
FIG. 6 shows substantially simplified representations of various impact frames with multiple frame sections.

In specific terms, the impact frame 14 according to the second embodiment of the impact frame may be created if the impact frame 14 comprises a frame element which is curved in a C-shape or a U-shape, the end sections of which form the first and second legs, wherein one leg is longer than the other leg, the first connection device is arranged on the end of the longer leg, and the second connection device is arranged on the end of the shorter leg. However, since it is more flexible and can be used in a greater range of applications, it is preferred if the impact frame 14 comprises a plurality of frame sections, wherein the first and second legs form two frame sections which are connected to each other either directly or, preferably, via (at least one) further frame section(s), which extend at least in part in the direction that is defined by the first or second axis. The ends of the first and the second legs preferably extend substantially perpendicularly to the first and second axes. The individual frame sections may be straight or curved (as in FIG. 1) and may have the form of elongated metal elements. FIG. 6 shows highly simplified representations of impact frames 14 with 3, 4 and 5 Frame sections. If multiple straight frame sections are arranged accordingly, or if curved frame sections are used, the resulting impact frame substantially corresponds to a particularly preferred C-shape.

The frame sections are preferably connected to each other in fixed or rigid manner, to ensure that the impact frame is of sufficient stiffness. Alternatively, the frame sections may be connected to each other in such manner as to be adjustable and fixable, e.g., by means of screw connections, thereby enabling the shape of the impact frame 14 to be changed and adapted to various tool heads and clamping assemblies. The impact frame may further be furnished with possible attachment means, e.g., recesses or holes, for a handle for holding the impact frame or the surgical instrument (see for example FIG. 5*e*, FIG. 5*f* and FIG. 5*g*).

There are very many different possibilities for creating each of the connection devices (first, second and third), e.g., threaded connections, clamping connections, tongue-and-groove systems, bayonet catches, etc. In one preferred, at least one (preferably both) connection device(s) has/have a passthrough hole 30 in the impact frame 14, which hole extends in the direction of the first or second axis; the clamping assembly and the impacting device is then fastened by inserting for example a screw or a threaded bolt through the respective passthrough hole and screwing it tight.

Figure 3:
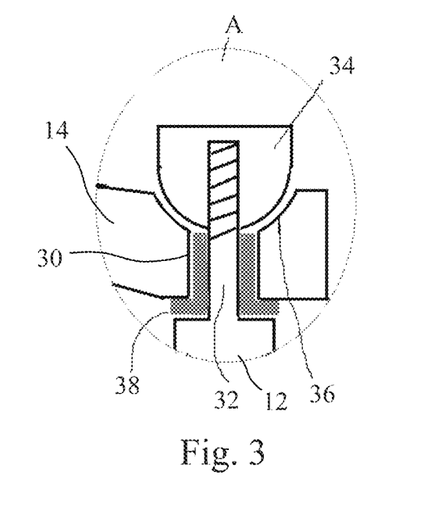
FIG. 3 shows an inset from FIG. 1 with a connection device.

This is shown for example in FIG. 3 in inset A from FIG. 1. A connection screw 32 which is connected to the clamping assembly or integrated therein is inserted through the passthrough hole 30 in the impact frame 14. Connection screw 32 is tightened in place on the impact frame 14 with a nut 34, shown in the figure as a hemispherical nut, for example, which is supported in a hemispherical nut bed 36. An elastomer bushing (elastomer ring) 38 is also arranged in the passthrough hole 30 and surrounds the connection screw 32 in order to damp transversely acting forces, since a hammer blow for example is normally struck slightly obliquely and then also exerts a force transversely to the lengthwise direction; this is indicated in FIG. 1 by a diagram 46 of force vectors. The elastomer bushing 38 is preferably made from silicone or includes silicone. Thus, in this case the connection device is formed by an assembly, and the resulting system is a connecting device complex, as it were.

The connection device of the embodiment according to FIG. 3 is non-fixed in the sense that the connection created thereby is elastic in some directions (e.g., transversely to the axis of the connection device); it is fixed conditionally so to speak—depending on the direction of the force applied. In this context, connection devices or connectors are also possible which are fixed, i.e., not elastic (or with any damping effect) in any direction. For example, a threaded connection without an elastomer bushing or other elastic element. Non-detachable connections are also conceivable; for example, the clamping assembly and/or the impacting device may be soldered or welded to the impact frame. However, detachable connection devices or connectors are preferred.

Figure 4:
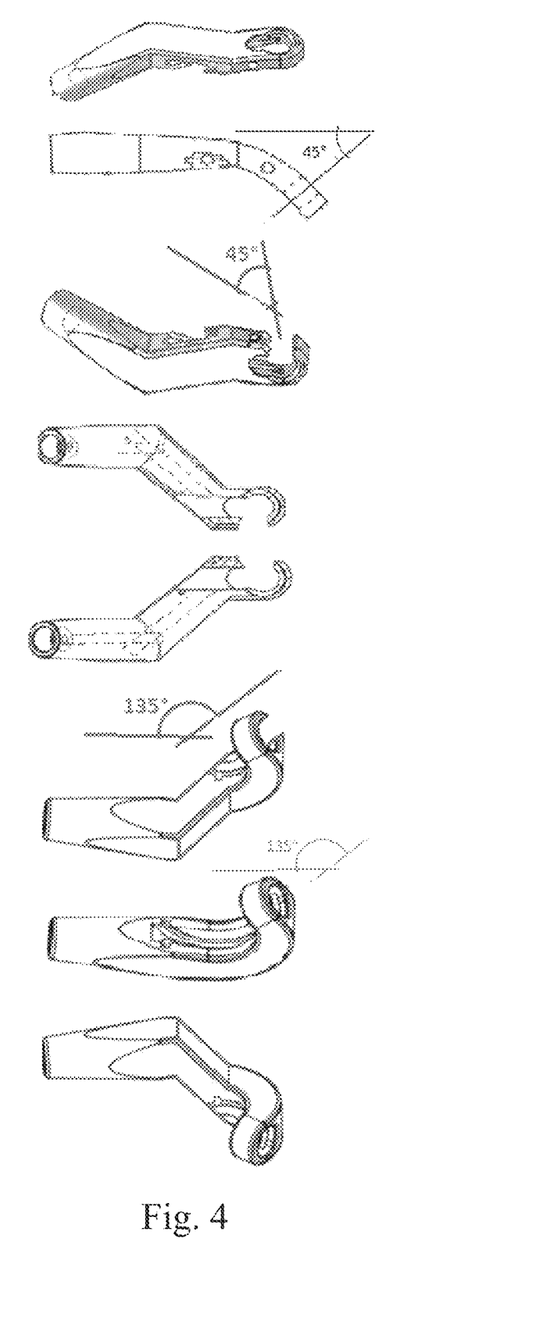
FIG. 4 shows examples of tool heads.

FIG. 4 shows various examples of tool heads, all of which have a lateral offset, except the second from bottom which has an upward offset. In some of the examples, the respective passthrough is open at the side. Various angles (45°, 135°) between the passthrough axis and the axis of the chuck are also indicated. Examples are also illustrated (1st and 3rd images and 4th and 5th images) which differ only in that the offset is made in different directions (to the left, the right, upwards) relative to a frontal view: these directions each refer to the illustrations in the figure). It is possible to use all these different tool heads together with the impact frame of the present invention.

Figures 5, 5A, 5J:
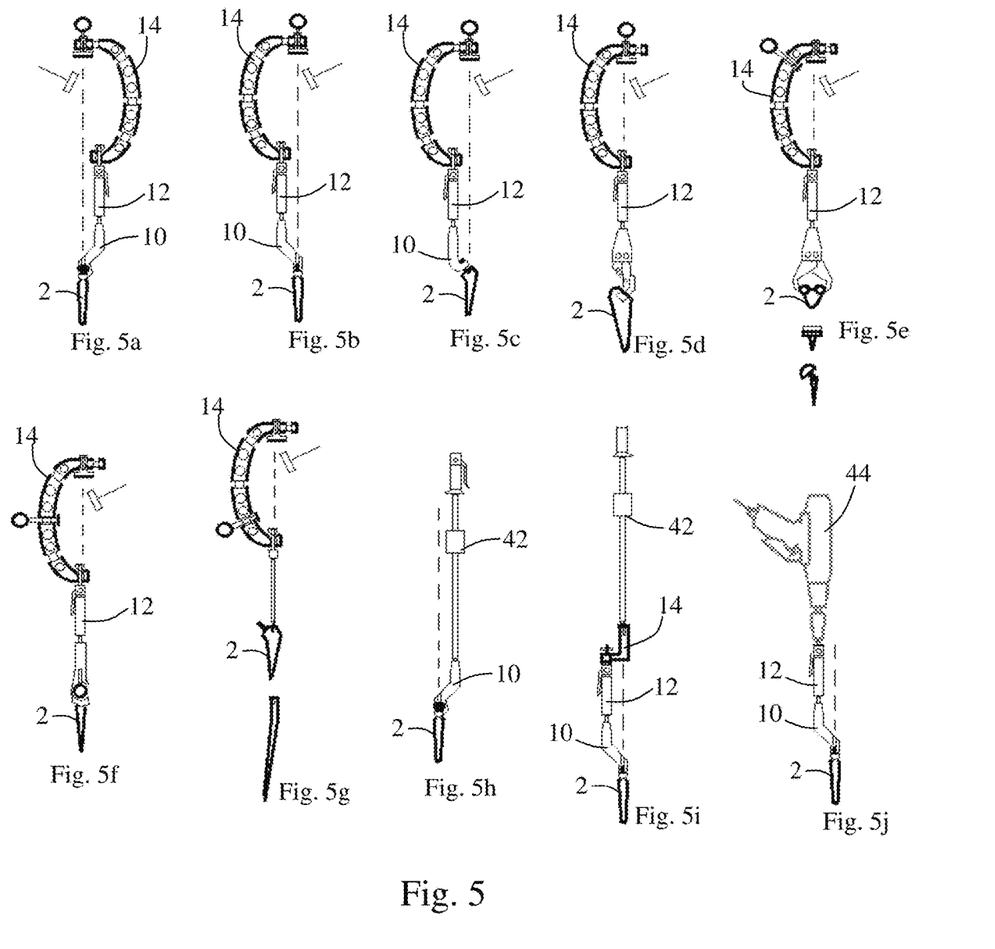
FIG. 5 shows various designs of modular surgical instruments in detail figures FIG. 5*a*-FIG. 5*j*.

FIG. 5, which includes thumbnail figures FIG. 5a-FIG. 5j, represents surgical instruments in various configurations. The figure is intended particularly to illustrate the modular nature of the surgical instrument according to the present invention, and the possibilities for use resulting therefrom with various prostheses and for different access methods. FIG. 5a, FIG. 5b and FIG. 5c show the use of different tool heads 10 according to the invention, which have a lateral offset, wherein the impact frame 14 and the clamping assembly 12 are both used. FIG. 5d, FIG. 5e, FIG. 5f and FIG. 5g illustrate the use of an impact frame 14 which is equipped with the third connection device (in this case a passthrough hole in the impact frame), wherein in each case a tool head (known in the related art) without a lateral offset is used. In FIG. 5d and FIG. 5e, the respective prosthesis 2 is grasped with a spreader forceps (FIG. 5d) or clamping tongs (FIG. 5e). In FIG. 5f, a straight tool head with laterally open passthrough is used. In FIG. 5g, the prosthesis 2 is connected to a rod by a threaded connection, which rod is connected to the impact frame 14 at the second connection device. In these cases (FIG. 5d, FIG. 5e, FIG. 5f and FIG. 5g) the impact force is produced by means of an impact plate 16 (and a hammer), which is connected to the third connection device. In FIG. 5e and FIG. 5g, further prosthesis types are indicated below the prosthesis 2 that is connected to the surgical instrument. FIG. 5h shows the user of a tool head with lateral offset, wherein the impact force is created with a slide hammer 42 with integral clamping assembly, the hammer being connected directly to the tool head 10. FIG. 5i shows the use of a tool head 10 with lateral offset and an L-shaped impact frame 14, wherein the impact force is generated with a slide hammer 42 that is connected to one leg of the L-shape, and a clamping assembly 12 is connected to the other leg of the L-shape. FIG. 5j shows the use of a tool head 10 with lateral offset, wherein the impact force is generated with a pneumatic impact machine 44 which is connected to the tool head 10 via a clamping assembly 12. In the arrangements according to FIG. 5h and FIG. 5j, the axis of the impact force effect is not coincident with the prosthesis axis (which is the same as the knocking-out axis), so transverse forces may arise during knocking out.

Figure 7:
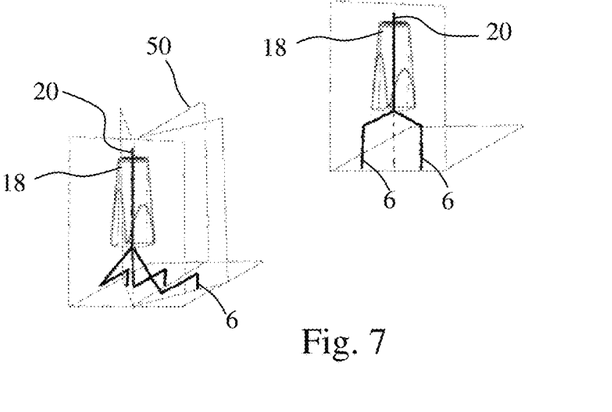
FIG. 7 illustrates shift planes.

FIG. 7 shows the "offset planes" in highly simplified form. Part of the tool head is shown here, wherein chuck 18 and axis 20 thereof are shown in particular. The prosthesis axis 6 at a distance from the axis 20 of chuck 18 is also represented, wherein the prosthesis axis with a lateral offset is located outside of the plane 50 defined by the passthrough axis and the lengthwise direction, or in one case, in the thumbnail image at bottom left, within this plane (corresponding to the tool head shown in the second image from the bottom in FIG. 4). The axes shown in the top right thumbnail diagram correspond to tool heads in which the angle between the passthrough axis and the lengthwise direction is approximately 45°, in the bottom left thumbnail this angle is approximately 135°.

In summary, the tool head 10 and the impact frame 14 are preferably aligned so that not only is the first axis 54 is coincident with the prosthesis axis 6 but also the second axis 58 is coincident with the axis 20 of chuck 18 and, where applicable with the third axis 62, wherein the first and second axes are at a distance from each other; in this way it is possible to enable a minimally invasive operation and to ensure that force is exerted along the prosthesis axis.

The invention claimed is:
1. A modular surgical instrument for knocking out or implanting a prosthesis,
wherein the prosthesis has a prosthesis axis and a prosthesis neck that defines a prosthesis neck axis which extends in a direction not parallel to the prosthesis axis,
the modular surgical instrument comprising:
a tool head with a passthrough for accommodating the prosthesis neck,
a locking device configured for locking the prosthesis neck in the passthrough,
a chuck for transferring a clamping force to the locking device, the chuck having an axis
extending in a lengthwise direction,
a clamping assembly detachably connected to the tool head at the chuck and having a
clamping element for applying a clamping force,
an impact frame detachably connected to the clamping assembly and having a first
connection device with a first axis, and
an impacting device attached to the first connection device for transferring an impact
force,
wherein the passthrough and the chuck are arranged on opposite ends of the tool head
relative to the lengthwise direction,
wherein the passthrough defines a passthrough axis which coincides with the
prosthesis neck axis when the prosthesis neck is positioned to be locked to the tool
head; and
wherein the chuck axis is parallel to and at a distance from the prosthesis axis when
the prosthesis neck is positioned to be locked to the tool head.
2. The modular surgical instrument according to claim 1, wherein the distance is in the range from 2 cm-20 cm.
3. The modular surgical instrument according to claim 1, wherein the locking device comprises a blocking element which engages in the passthrough to apply the clamping force to the prosthesis neck when the prosthesis neck is configured to be locked to the tool head, wherein the passthrough axis extends substantially perpendicularly to a direction of movement of the blocking element.
4. The modular surgical instrument according to claim 1, wherein the impacting device comprises an impact plate, a slide or a pneumatic impact machine and is configured such that the impact force is exerted along the first axis.
5. The modular surgical instrument according to claim 1, wherein the first connection device is arranged in the lengthwise direction when viewed from the passthrough, so that the first axis is coincident with the prosthesis axis when the prosthesis neck is positioned to be locked to the tool head.

6. The modular surgical instrument according to claim 1, wherein the impact frame further comprises a first leg and a second leg; wherein the first connection device is arranged on one end of the first leg for the impacting device; and wherein the modular surgical instrument further comprises a second connection device having a second axis and arranged on one end of the second leg for the clamping assembly; wherein a space remains free between the ends of the first and second legs in the direction of the first axis and the second axis; and wherein the first axis and the second axis are parallel to and at a distance from each other.

7. The modular surgical instrument according to claim 1, wherein the impact frame has an L-shape, wherein the clamping assembly is connected detachably to a second leg of the L-shape by means of a second connection device, and wherein the first connection device is arranged on a first leg of the L-shape for the impacting device.

8. An impact frame for knocking out or implanting a prosthesis, wherein the prosthesis has a prosthesis axis and a prosthesis neck that defines a prosthesis neck axis that extends in a direction not parallel to the prosthesis axis, the impact frame comprising:

a first leg and a second leg forming first and second frame sections, and a third frame section connecting the first and second legs;

a first connection device with a first axis arranged through an end of the first leg and receiving an impacting device;

a second connection device with a second axis that is parallel to the first axis and arranged through an end of the second leg, parallel to the second axis, and receiving a clamping assembly;

a third connection device with a third axis coincident with the second axis; and an impact plate attached to the first connection device or the third connection device;

wherein the ends of the first leg and the second leg are spaced apart in a direction defined by the first and second axes and extend substantially perpendicularly to the first and second axes, wherein the third frame section extends in the direction defined by the first and the second axes, and wherein the first connection device or the second connection device or the third connection device comprises a passthrough hole in the impact frame, an elastomer bushing arranged in the passthrough hole, and a connection screw which extends through the passthrough hole and is fastened by means of a hemispherical nut which is supported in a hemispherical nut bed on the impact frame.

9. The impact frame according to claim 8, wherein a distance between the first axis and the second axis is in the range from 0 cm-20 cm.

\* \* \* \* \*